(12) United States Patent
Foster et al.

(10) Patent No.: US 8,893,884 B2
(45) Date of Patent: Nov. 25, 2014

(54) SHARPS CONTAINER

(75) Inventors: Derick Foster, Huntington Beach, CA (US); Cynthia R. Meissen, Atlanta, GA (US); Ryan C. Meers, West Chester, PA (US); Margaret McCanless, El Segundo, CA (US)

(73) Assignee: Rehrig Pacific Company, Los Angeles, CA (US)

( * ) Notice: Subject to any disclaimer, the term of this patent is extended or adjusted under 35 U.S.C. 154(b) by 135 days.

(21) Appl. No.: 13/241,091

(22) Filed: Sep. 22, 2011

(65) Prior Publication Data

US 2012/0067753 A1 Mar. 22, 2012

Related U.S. Application Data

(60) Provisional application No. 61/385,539, filed on Sep. 22, 2010, provisional application No. 61/422,776, filed on Dec. 14, 2010, provisional application No. 61/513,378, filed on Jul. 29, 2011.

(51) Int. Cl.
*B65D 83/10* (2006.01)
*A61B 19/02* (2006.01)

(52) U.S. Cl.
CPC ..... *A61B 19/0288* (2013.01); *A61B 2019/0206* (2013.01); *A61B 2019/0245* (2013.01); *A61B 2019/0275* (2013.01); *A61B 2019/0277* (2013.01); *Y10S 220/908* (2013.01)
USPC ..................... 206/366; 220/254.3; 220/908

(58) Field of Classification Search
USPC .......... 206/363–370; 220/810, 825, 908, 252, 220/254.1, 254.3
See application file for complete search history.

(56) References Cited

U.S. PATENT DOCUMENTS

| | | | | | |
|---|---|---|---|---|---|
| 4,715,498 | A | * | 12/1987 | Hanifl | 206/366 |
| 5,076,429 | A | * | 12/1991 | Patrick et al. | 206/366 |
| 5,178,322 | A | * | 1/1993 | Shillington | 206/366 |
| 5,387,735 | A | * | 2/1995 | Ponsi et al. | 206/366 |
| 6,889,831 | B2 | * | 5/2005 | Pike | 206/366 |
| 7,596,844 | B2 | * | 10/2009 | Japuntich et al. | 206/366 |
| 2008/0067092 | A1 | * | 3/2008 | Finnestad et al. | 206/366 |

* cited by examiner

*Primary Examiner* — Luan K Bui
(74) *Attorney, Agent, or Firm* — Carlson, Gaskey & Olds

(57) ABSTRACT

A sharps container includes a sub-lid that normally defines an opening into the container that is too small for a hand. Upon closure of the sub-lid, the opening is enlarged so that larger objects can be placed in the container while the closure of the sub-lid continues to prevent a hand from reaching into the container interior. Other embodiments are also disclosed.

23 Claims, 21 Drawing Sheets

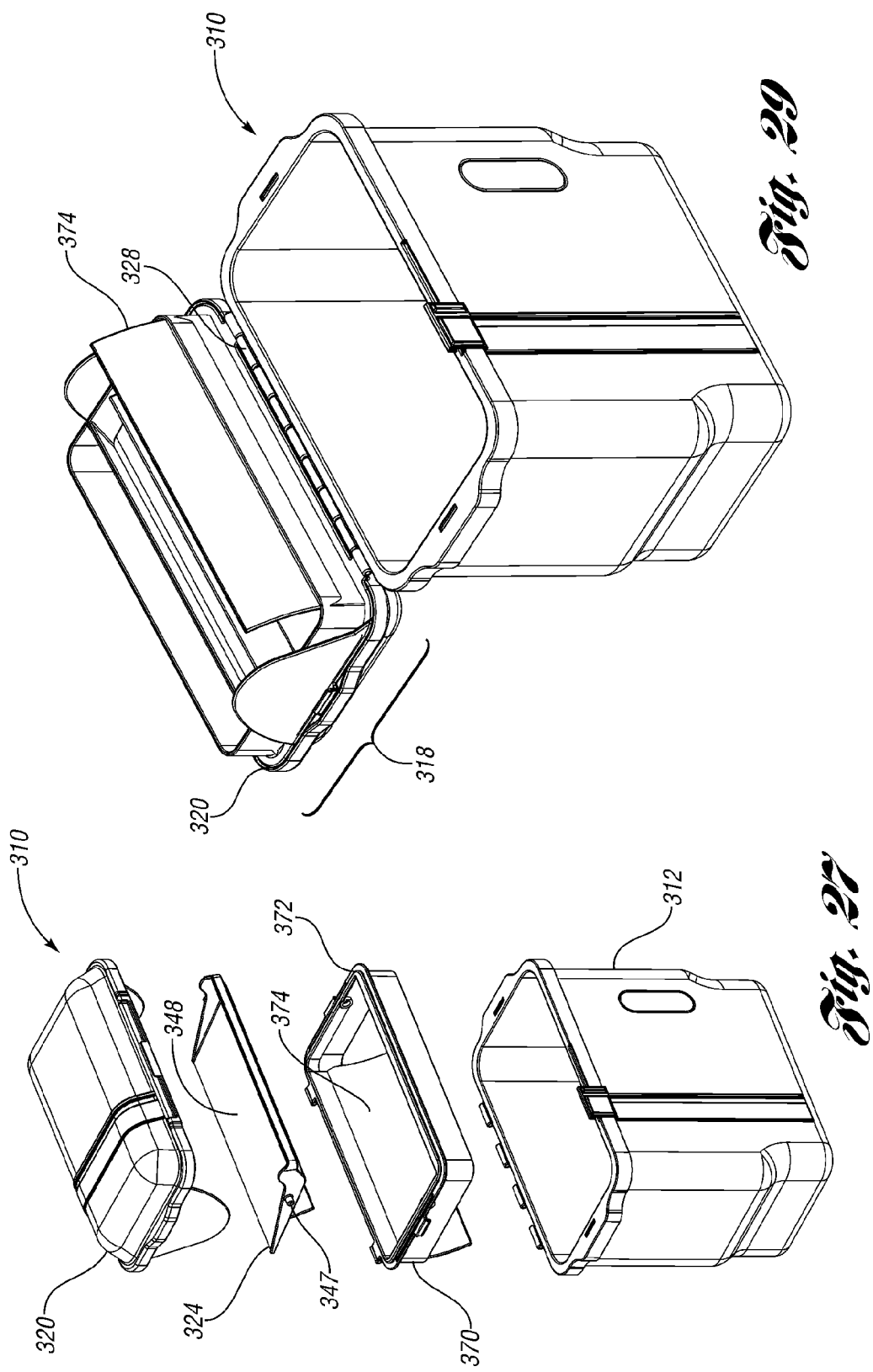

SHARPS CONTAINER

This application claims priority to U.S. Provisional Application Ser. Nos. 61/385,539, filed Sep. 22, 2010; 61/422,776, filed Dec. 14, 2010; and 61/513,378, filed Jul. 29, 2011.

BACKGROUND

Sharps containers are used in hospitals, doctor offices and other areas for the safe disposal of needles and other sharp objects. Some sharps containers inhibit the ability of a person to reach a hand into the container where the hand could come into contact with the sharps.

Some sharps containers may simply include an opening too small for a hand; however these sharps containers cannot accommodate the occasional large object.

SUMMARY

Several different embodiments of sharps containers are disclosed herein. In a first embodiment, the sharps container includes a sub-lid that normally defines an opening into the container that is too small for a hand. Upon closure of the sub-lid, the opening is enlarged so that larger objects can be placed in the container while the closure of the sub-lid continues to prevent a hand from reaching into the container interior.

BRIEF DESCRIPTION OF THE DRAWINGS

FIG. 27 is an exploded view of the container of FIG. 25.

FIG. 29 shows the container of FIG. 25 with the lid assembly pivoted to the open position for cleaning.

DETAILED DESCRIPTION OF THE PREFERRED EMBODIMENT

Figure 1:
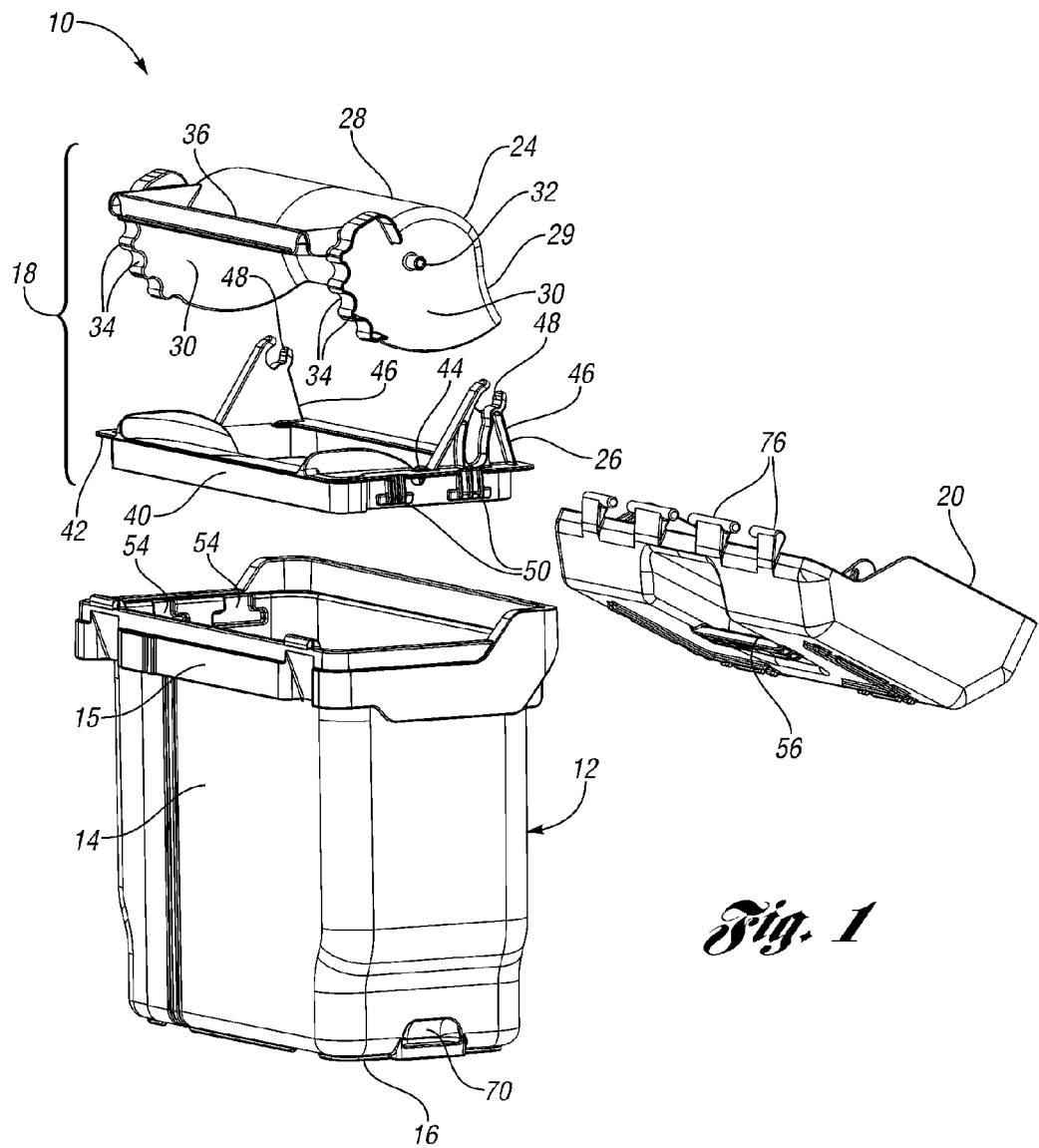
FIG. 1 is an exploded view of a sharps container according to a first embodiment.

An exploded view of a sharps container 10 according to one embodiment of the present invention is shown in FIG. 1. The sharps container 10 includes a body portion 12 having a side wall 14 extending upwardly from the perimeter of a base wall 16. A lip 15 protrudes outwardly and then downwardly from an upper edge of the side wall 14. The container 10 further includes a lid assembly 18 selectively enclosing the opening to the body portion 12. The lid assembly 18 includes a lid 20, a sub-lid 24 and an insert 26.

The sub-lid 24 includes a concave upper wall 28 and a rear wall 29 between two side walls 30 having pivot pins 32 projecting outwardly therefrom. Crenulated or corrugated handle portions 34 project outwardly from a front edge of the side walls 30. A flange 36 projects forward from the concave upper wall 28.

The insert 26 includes a peripheral wall 40 and a lip 42 projecting outwardly from an upper edge of the peripheral wall 40. Recesses 44 are formed on the interior of the insert 26 for pivotably receiving the pivot pins 32 of the sub-lid 24. Brackets 46 project upwardly from lateral edges of the insert 26 toward the rear of the insert 26. Each bracket 46 includes a guide track 48 having a narrow portion spaced away from an open end. Connectors 50 project downwardly at each lateral end of the insert 26 for connecting the insert 26 to the body portion 12.

The body portion 12 includes complementary recessed connectors 54 for receiving the connectors 50 of the insert 26. The body portion 12 may optionally be molded from a translucent polymer so that it can be determined whether the container 10 is full. Indentations 70 are formed in each lateral portion of the side wall 14 of the body portion 12 so that the body portion 12 can be locked to a counter top.

A handle 56 may be integrally molded with the lid 20. Hinge pins 76 are formed along a rearward edge of the lid 20 for connection to the body portion 12.

Figure 2:
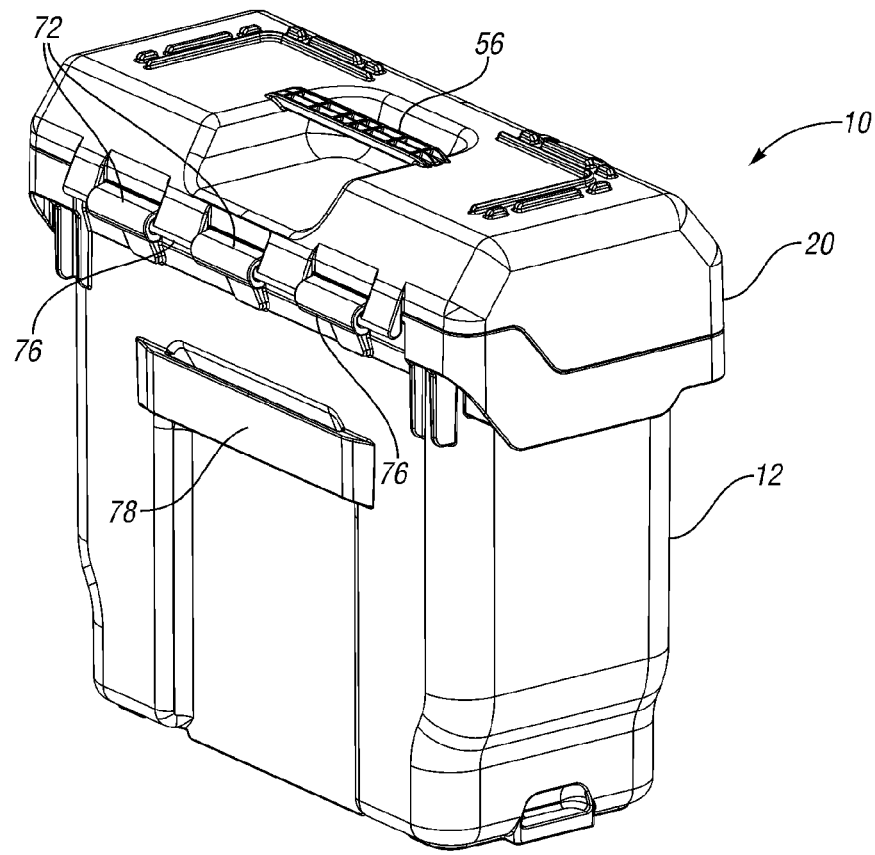
FIG. 2 is a rear perspective view of the assembled container of FIG. 1.

FIG. 2 is a rear perspective view of the assembled container 10 in a closed position. Hinge pin receivers 72 are formed along a rearward side of the lip 15 for hingeably connecting the hinge pins 76 of the lid 20 to the body portion 12. A bracket 78 across the rear of the body portion 12 can be used to lock the container 10 to a wall mount.

Figure 3:
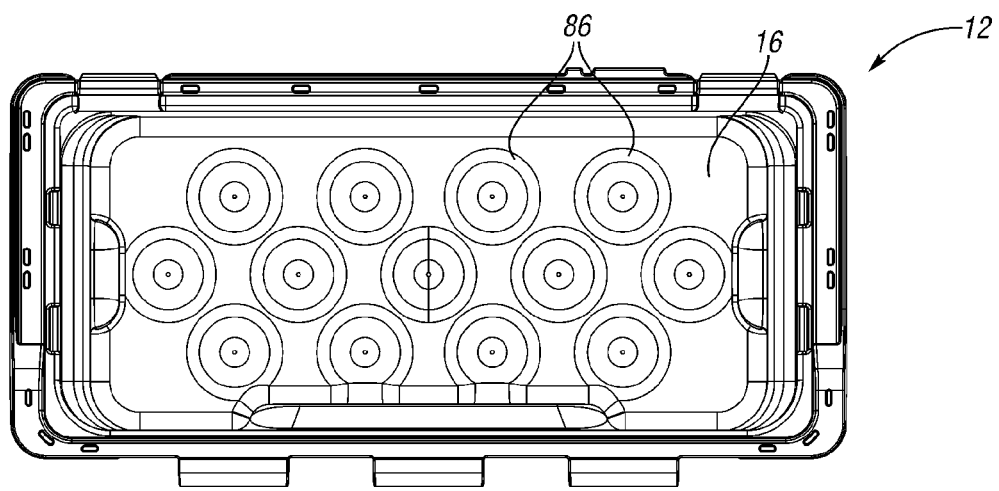
FIG. 3 is a top view of the body portion of the container of FIG. 1.

FIG. 3 is a top view of the body portion 12. As shown, the base 16 includes a plurality of soft bumps 86 that keep waste from sticking to the base 16.

Figure 4:
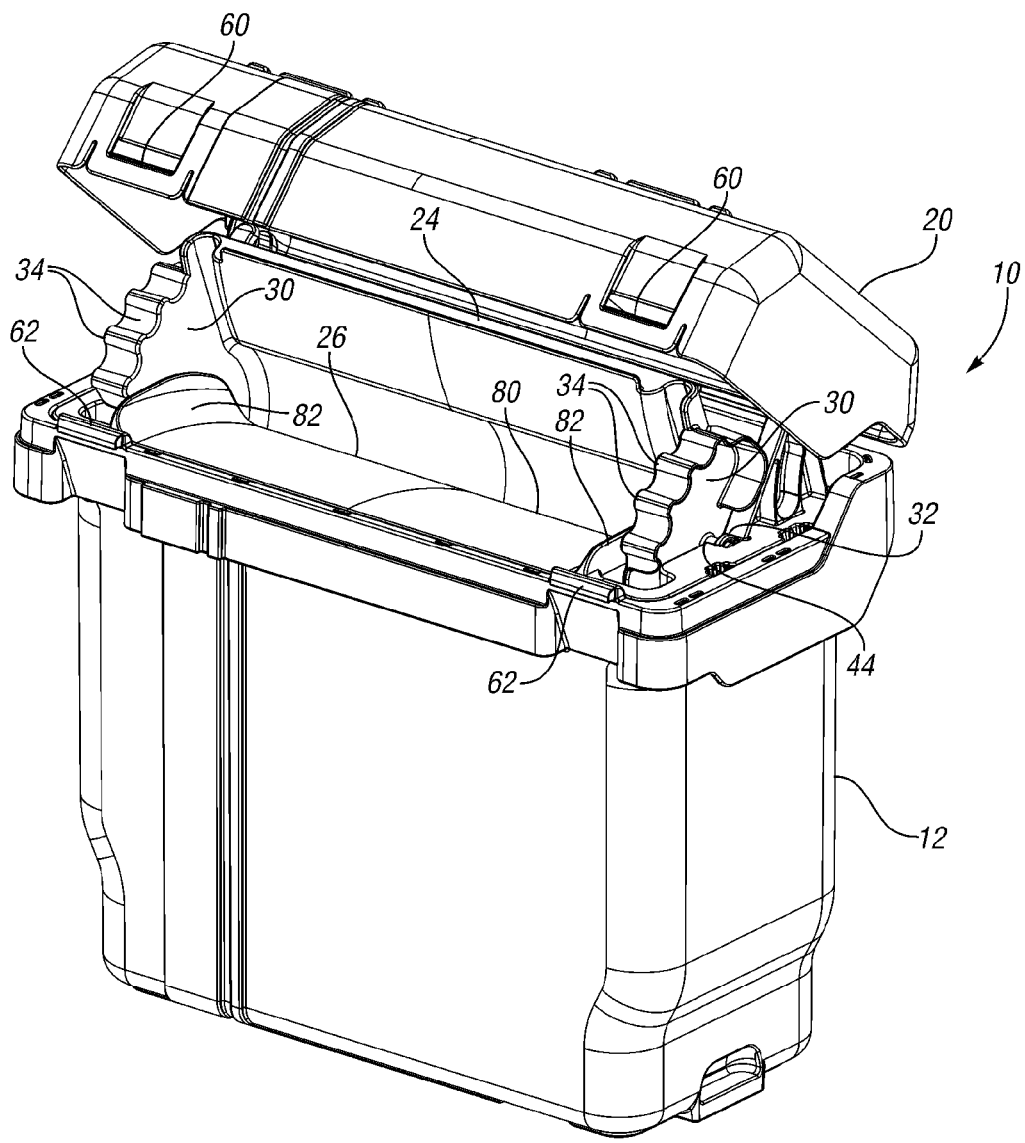
FIG. 4 is a perspective view of the container of FIG. 2 in the open, use position.

FIG. 4 shows the assembled container 10 in the open position. The insert 26 includes an apron 80 angling downwardly from an upper front edge of the insert 26. The apron 80 has upwardly angled side edges 82. The handles 34 and side walls 30 of the sub-lid 24 are disposed outwardly of the side edges 82 of the apron 80 of the insert 26. The pivot pins 32 of the sub-lid 24 are received in the recesses 44 of the insert 26 so that the sub-lid 24 is pivotably mounted in the insert 26. The front edge of the lid 20 includes a pair of latch openings 60 for interlocking with tabs 62 on the lip 15 of the body portion 12 to lock the lid 20 to the body portion 12. A gasket (not shown) may optionally be secured to the lid 20 to seal liquids within the container 10.

Figure 5:
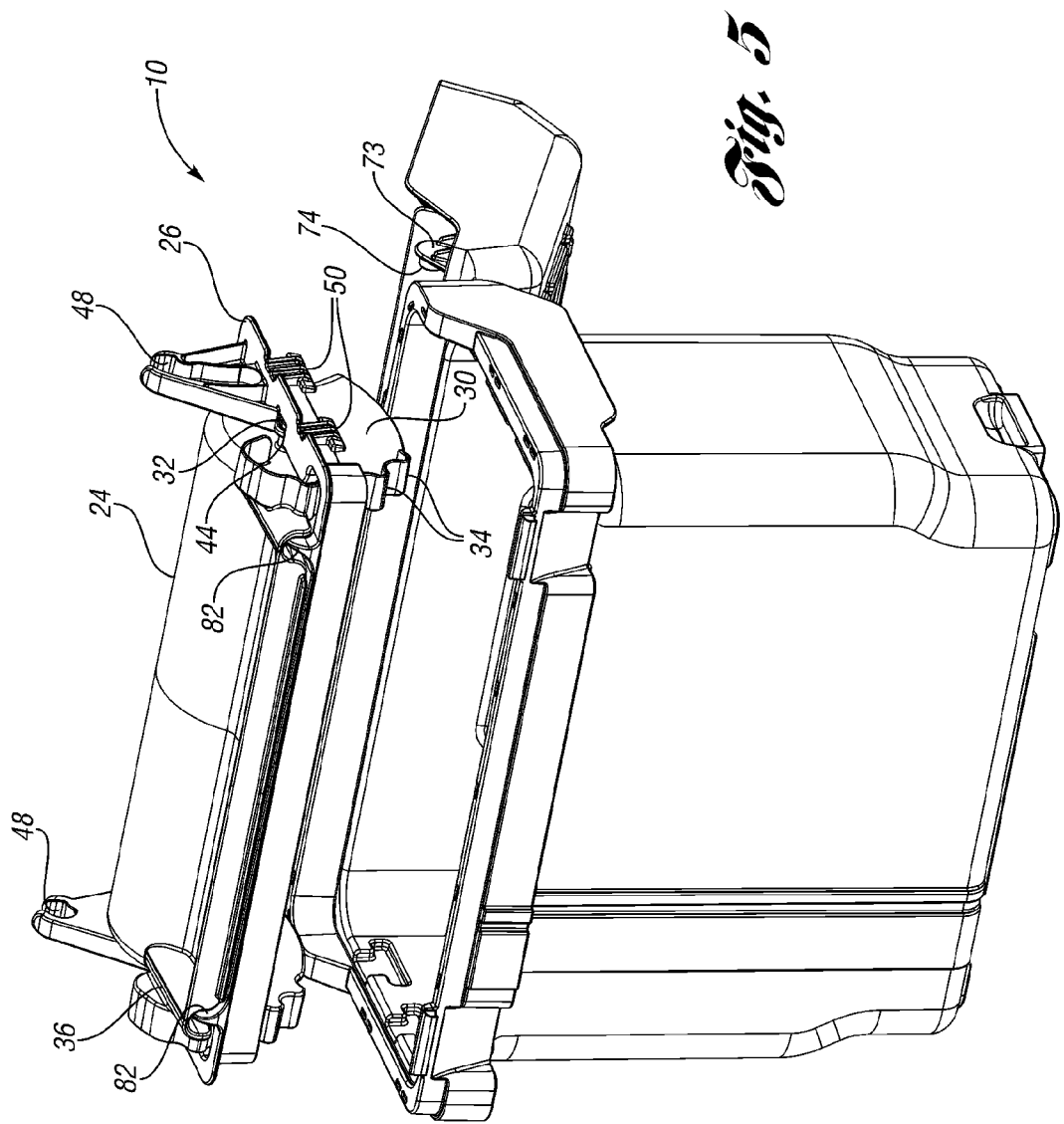
FIG. 5 is a perspective view of the assembly of FIG. 4, with the insert 26 and sub-lid 24 removed from the body portion

FIG. 5 is a perspective view of the assembly of FIG. 4, with the insert 26 and sub-lid 24 removed from the body portion 12. The sub-lid 24 is shown in a closed position, with the angled side edges 82 of the apron 80 of the insert 26 received in recesses in the front flange 36 of the sub-lid 24.

Figure 6:
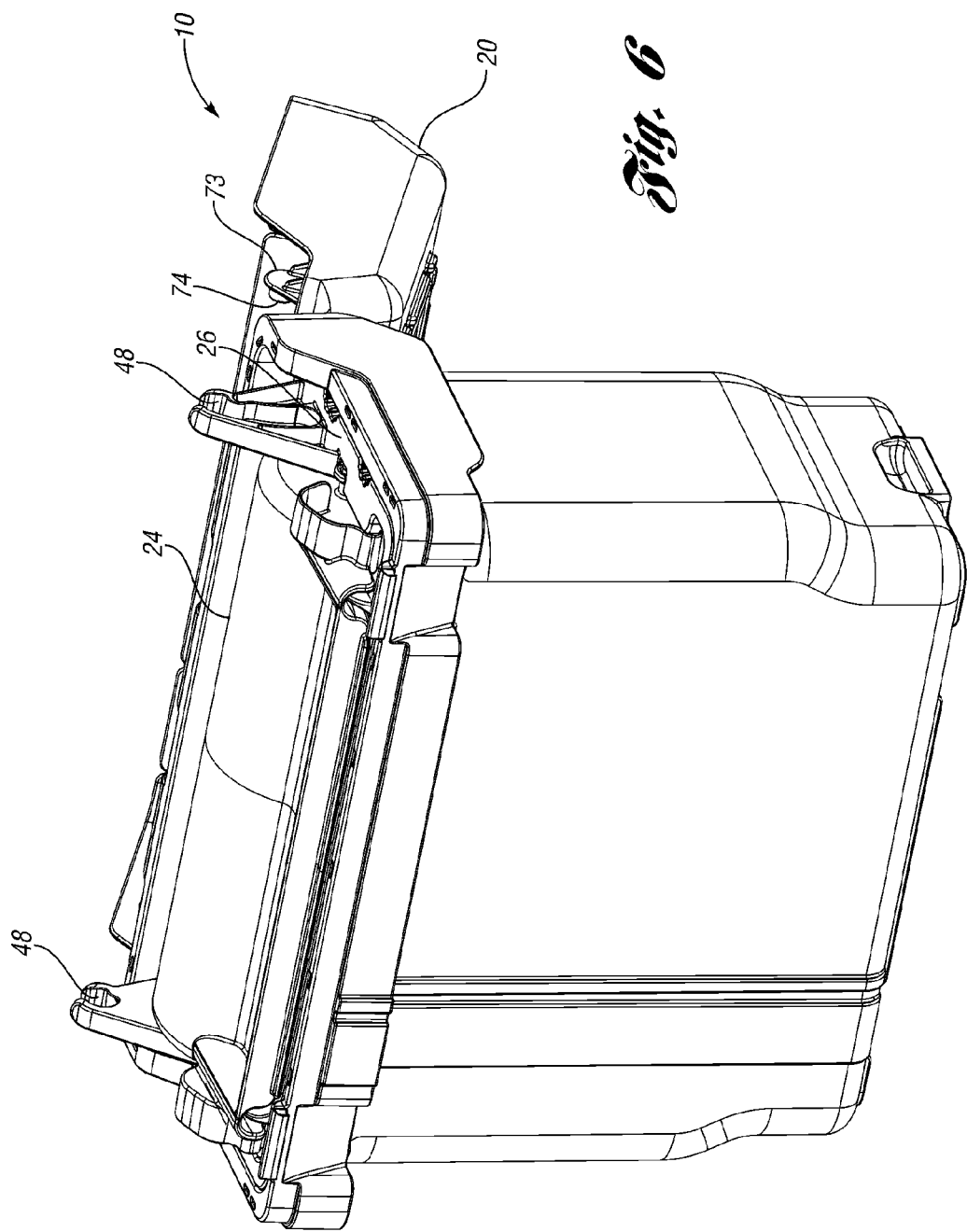
FIG. 6 shows the sub-lid 24 and insert 26 snap-fit into the body portion

FIG. 6 shows the sub-lid 24 and insert 26 snap-fit into the body portion 12 (via connectors 50, 54 (FIG. 1)). In FIG. 6, the sub-lid 24 is in the closed position. The lid 20 is pivoted rearward. Brackets 73 project downwardly from a lower surface of a top wall of the lid 20. Pivot pins 74 project inwardly from the brackets 73. The pivot pins 74 align with the tracks 48.

Figure 7:
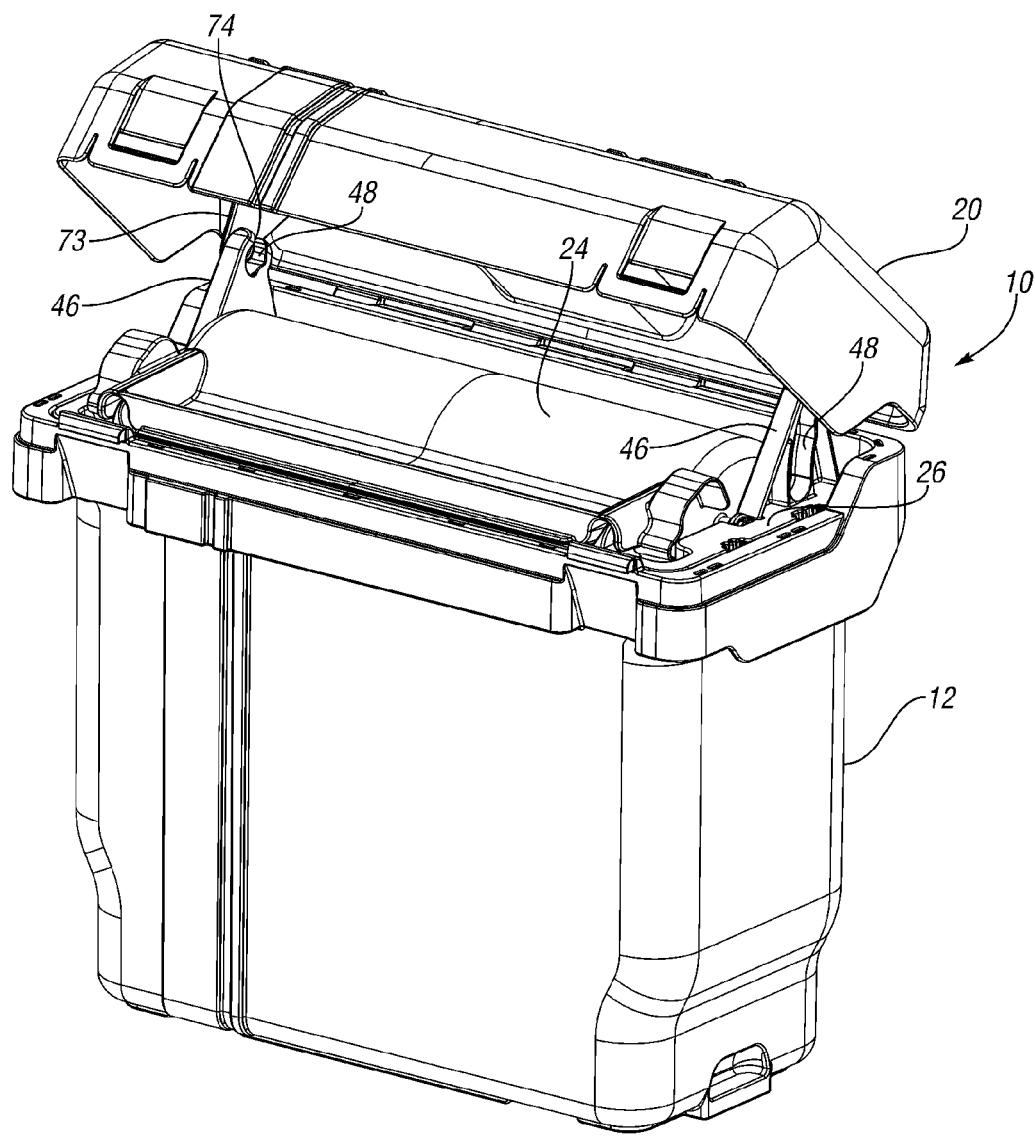
FIG. 7 shows the connection of the lid 20 to the insert

FIG. 7 shows the connection of the lid 20 to the insert 26. The pivot pins 74 snap-fit into an upper portion of the guide tracks 48 formed in the brackets 46 of the insert 26. The upper portion of the guide track 48 retains the pivot pins 74 in the upper portion until sufficient force is applied to the lid 20 to force the pivot pins 74 past the upper portion of the guide track 48 into the remainder of the guide track 48. In this manner, the lid 20 will remain in the open position during use until intentionally closed for transport when full.

Figure 8:
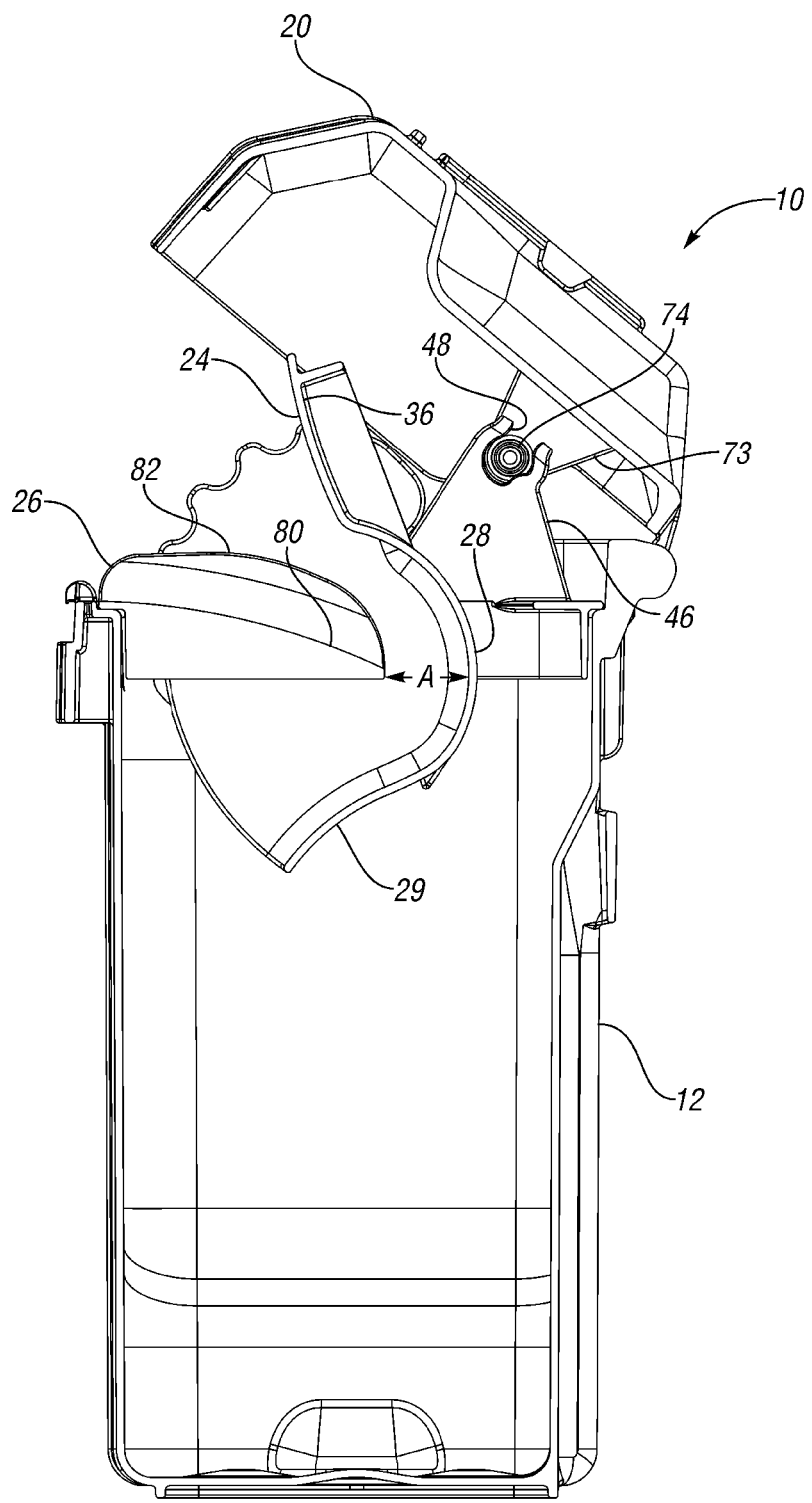
FIG. 8 is a section view of the container 10 of FIG. 7

FIG. 8 is a section view of the container 10 of FIG. 7. As shown, the hinge pins 74 snap-fit into the upper portion of the guide tracks 48 above the narrow portion formed in the brackets 46 of the insert 26. In FIG. 8, the sub-lid 24 is pivoted to the open position and the lid 20 is in the open position. In this position, a user can place an object (e.g. a sharp) on the apron 80 of the insert 26 and it will slide or roll toward the rear of the container 10, fall between the rearward edge of the apron 80 and the concave wall 28 of the sub-lid 24 onto the rear wall 29 of the sub-lid and then slide or roll forward into the container body portion 12.

The space between the rearward edge of the apron 80 and the concave wall 28 of the sub-lid 24 is shown as distance A in FIG. 8. This is the narrowest point in the path into the container 10 when the sub-lid 24 is open. In the example shown, the distance A is about 1.05", but other distances could be used. The distance A may be chosen small enough to prevent a user's hand from reaching into the container 10 when the sub-lid 24 is open, but large enough to let most objects fall into the body portion 12 without requiring the user to touch the container 10.

Figure 9:
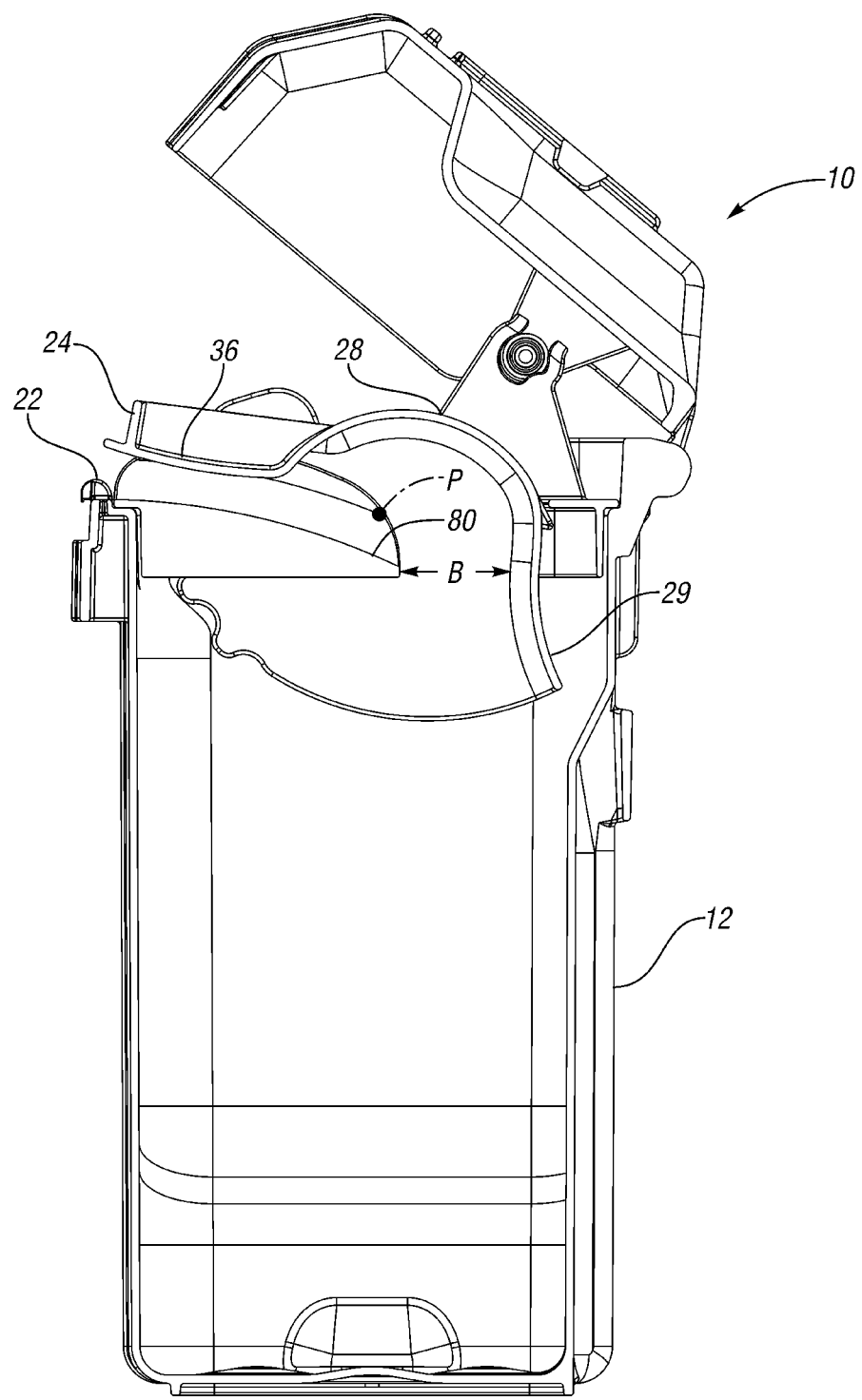
FIG. 9 shows the container of FIG. 8 with the sub-lid rotated forward.

If a larger object is placed on the apron 80, it may be larger than the distance A and therefore may stop at the rearward edge of the apron 80. In that case, the sub-lid 24 can be rotated forward as shown in FIG. 9. Because of the location of the pivot axis P (corresponding to pivot pins 32, more precisely identified in FIG. 1) of the sub-lid 24 and the shape of the sub-lid 24, the concave wall 28 and rear wall 29 move upward and rearward, thus enlarging the distance between the rearward edge of the apron 80 and the rear wall 29 to a distance B (FIG. 9, in this case about 1.58"). As the sub-lid 24 is pivoted forward, the larger object can drop into the body portion 12 of the container 10, but only as the sub-lid 24 is being closed, which prevents hand access into the body portion 12 of the container 10. When the sub-lid 24 is released, the weight of the rear wall 29 and concave wall 28 pivot the sub-lid 24 back to the open position.

Figure 10:
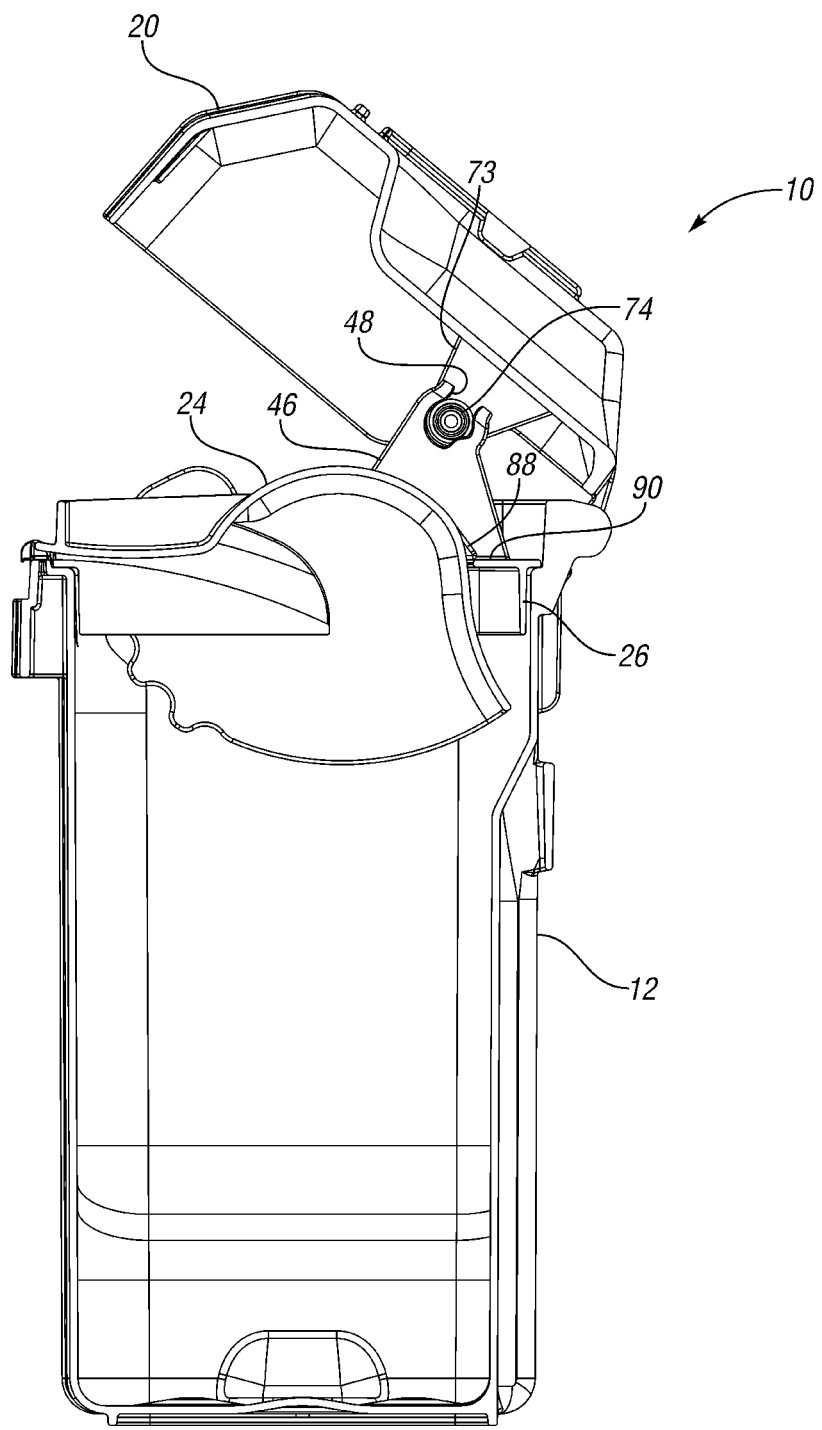
FIG. 10 shows the container of FIG. 8 with the sub-lid rotated forward to a locked position.
Figure 11:
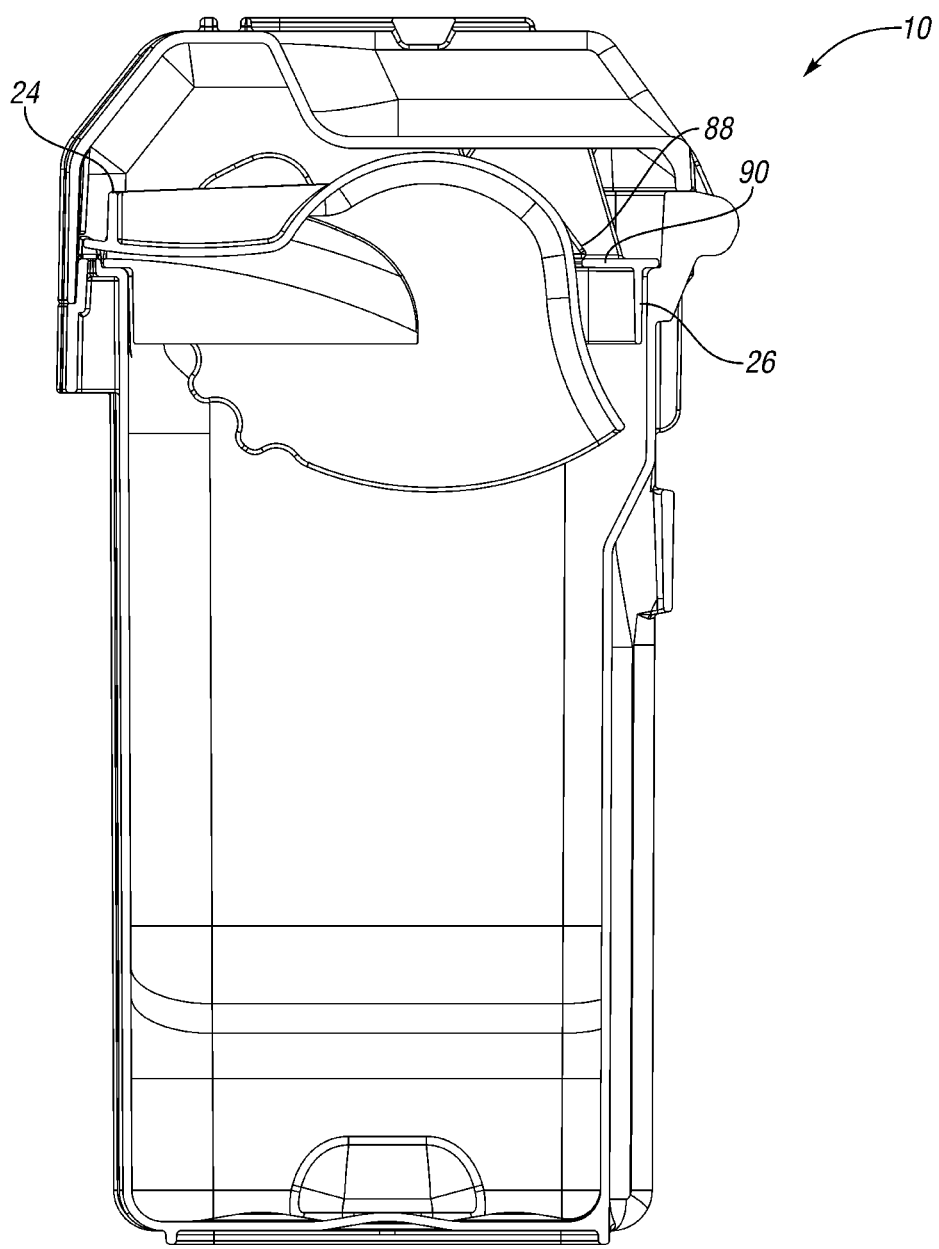
FIG. 11 shows the container of FIG. 10 with the lid closed.

As shown in FIG. 10, when the container 10 is full, the sub-lid 24 can be pivoted forward firmly, forcing a locking protrusion 88 on a rear surface of the sub-lid 24 past a flange 90 on the insert 26. This keeps the sub-lid 24 in the closed position. The lid 20 is then pivoted downward, forcing the pivot pins 74 into the tracks 48, until the lid 20 is closed, as shown in FIG. 11. When the lid 20 is closed, the tabs 62 on the lip 15 of the body portion 12 snap into the latch openings 60 on the lid 20 to keep the lid 20 in a closed position (tabs 62 and latch openings 60 shown in FIG. 4).

The closed container 10 can then be shipped to an appropriate facility for removing and disposing of the sharps, cleaning the container 10 and returning it to use.

Figure 12:
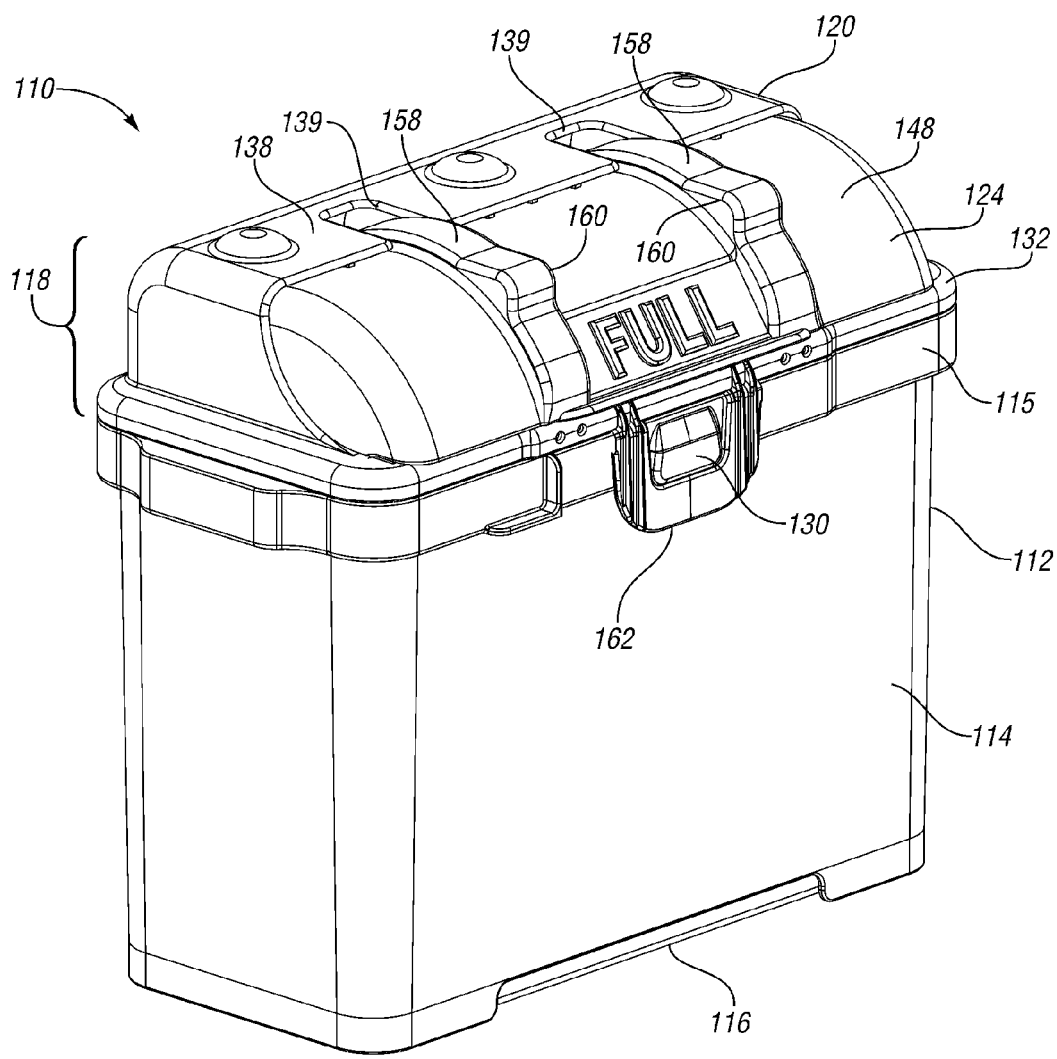
FIG. 12 is a perspective view of a container according to a second embodiment in a closed position.

A container 110 according to a second embodiment of the present invention is shown in FIGS. 12-19. Referring to FIG. 12, the container 110 includes a body portion 112 having a side wall 114 extending upwardly from a periphery of a base wall 116. A lip extends outwardly and then downwardly from an upper most edge of the side wall 114. A lid assembly 118 includes a lid portion 120 and a sub-lid 124. The lid portion 120 includes a hood 138 generally over a rearward half (approximately) of the opening to the container body portion 112. The hood 138 extends upwardly from rear and side portions of a lip portion 132 of the lid portion 120. The upper wall of the hood 138 includes a pair of openings 137. The sub-lid 124 includes a concave wall 148 having a pair of raised rail portions 158 along an exterior surface thereof, including an enlarged portion 160. The rail portions 158 are aligned with and received in the openings 137 of the hood 138.

Figure 14:
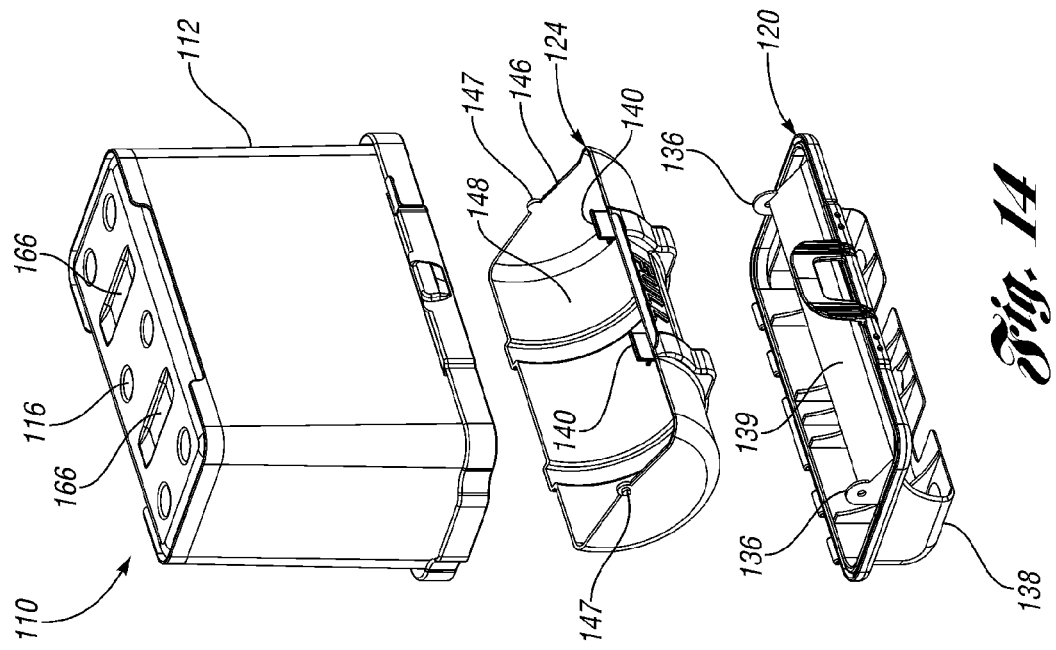
FIG. 14 is a bottom perspective view of the exploded container of FIG. 13.
Figure 13:
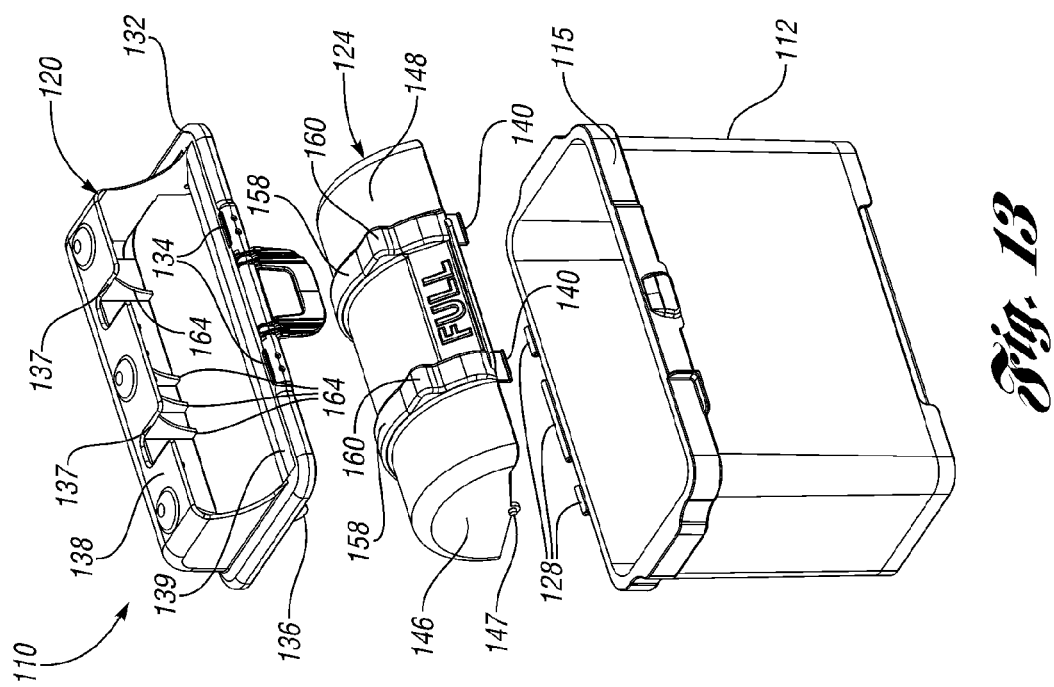
FIG. 13 is a perspective, exploded view of the container of FIG. 12.

FIGS. 13 and 14 are exploded views of the container 110. The lid portion includes a pair of slots 134 formed in a front portion of the lip 132. An upper wall 139 of the lid portion 120 extends rearwardly and downwardly from a front portion of the lip 132. The lid portion 120 further includes a pair of arms 136 extending downwardly adjacent the upper wall 139 to form pivot pin receiving portions. Concave ribs 164 are formed on a rear wall and the upper wall of the hood 138 of the lid portion 120.

The sub-lid 124 includes a concave wall 148, which in the embodiment shown is semi-cylindrical, although greater than or less than 180° could also be used. The sub-lid 124 also includes opposed side walls 146 from which hinge pins 147 protrude for pivotably connecting to the lid portion 120.

Hinge portions 128 are formed on a rear portion of the lip 115.

The front portion of the lip 115 includes a protruding latch portion 130, which snap-fit connects to a latch portion 162 formed integrally with the lid portion 120. The raised rail portions 158 provide more stable support for stacking another container on them when the sub-lid 124 is closed. Complementary recesses 166 in the bottom wall 116 of the body portion 112 receive the rail portions 158 when stacked thereon.

Figure 16:
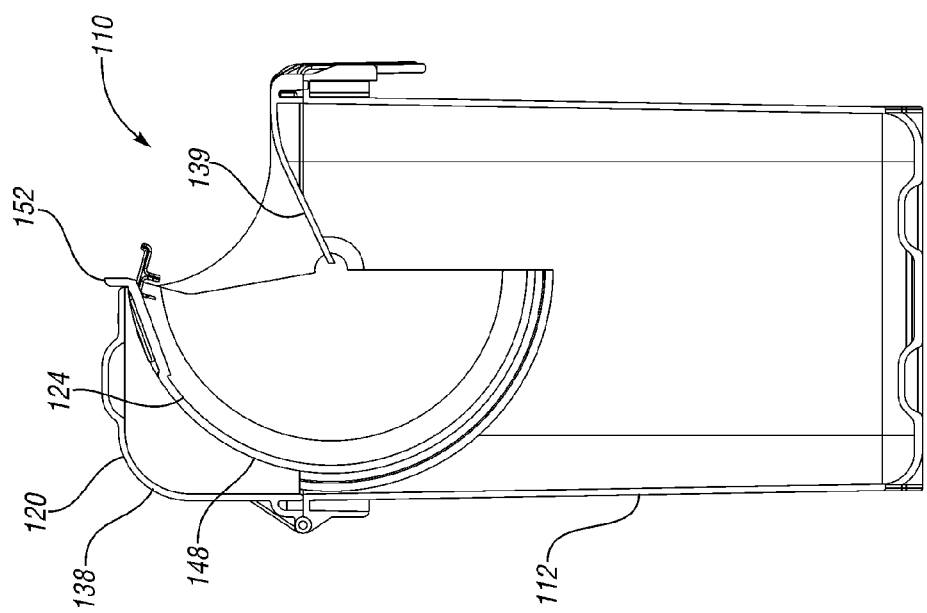
FIG. 16 is a section view through the container of FIG. 15.
Figure 15:
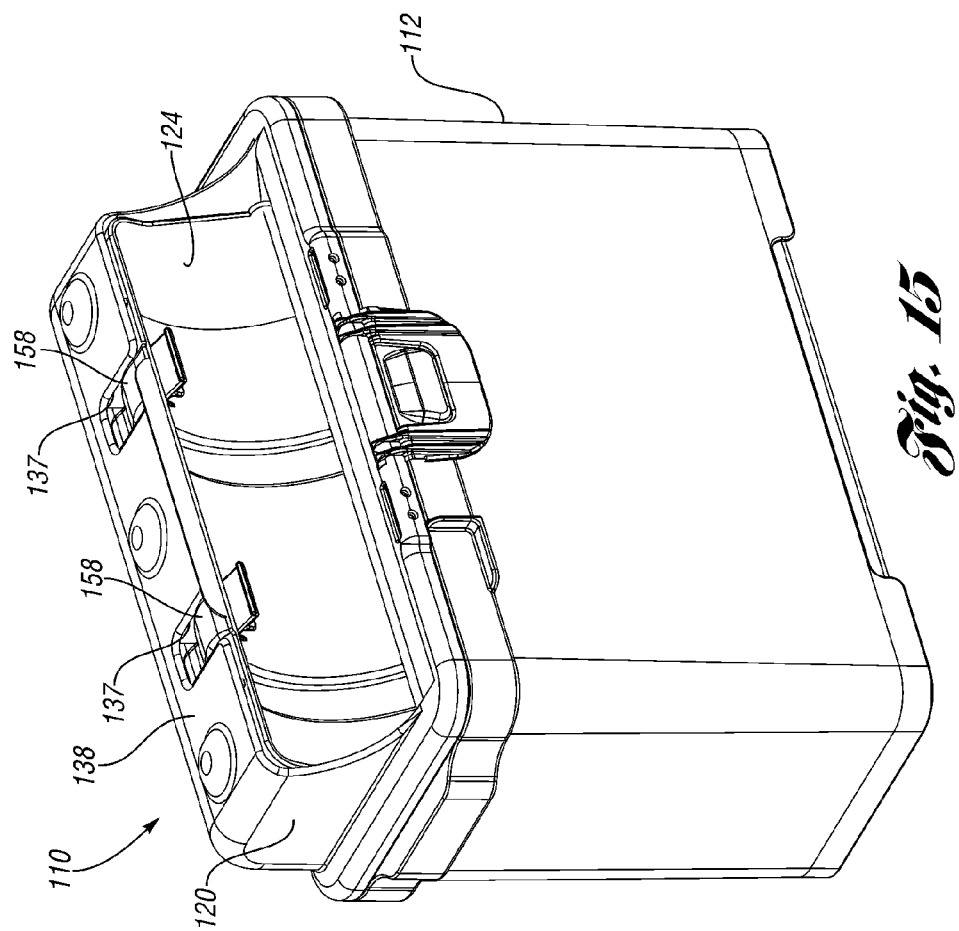
FIG. 15 shows the container of FIG. 12 with the sub-lid pivoted to an open position.

FIGS. 15 and 16 show the sub-lid 124 pivoted to the open position. As shown in FIG. 16, the flange 152 of the sub-lid 124 contacts the hood 138 of the lid portion 120 in the open position. The concave wall 148 of the sub-lid 124 together with the upper wall 139 of the lid portion 120 provide a tortuous path into the body portion 112 of the container 110. Objects can be dropped through the opening between the hood 138 and the upper wall 139 of the lid portion 120. If the object does not fall into the body portion 112 after rolling off the concave wall 148, the object will drop into the body portion 112 when the sub-lid 124 is rotated back to the closed position.

Figure 17:
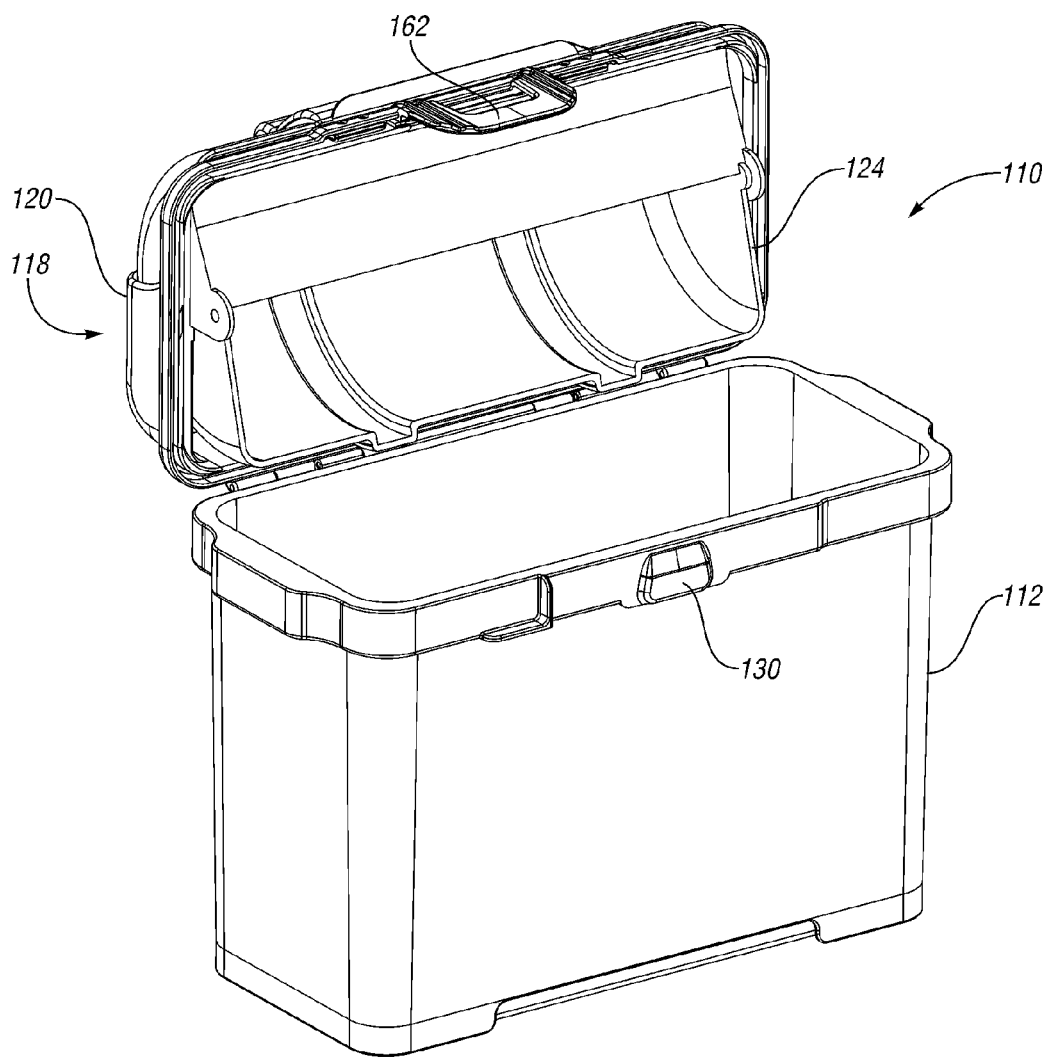
FIG. 17 shows the container of FIG. 12 with the lid assembly pivoted to an open position.

When full, the container 110 is shipped to a disposal facility in the closed position as shown in FIG. 12 with the locking tabs 140 snap-fit into the slots 134 in the lid portion 120 (FIGS. 13 and 14). At the disposal facility, the lid portion 120 is released from the body portion 112 by unlatching the latch portions 130, 162 and pivoting the lid assembly 118 to the open position, as shown in FIG. 17. The container is then emptied and washed before being returned for reuse.

Figure 19:
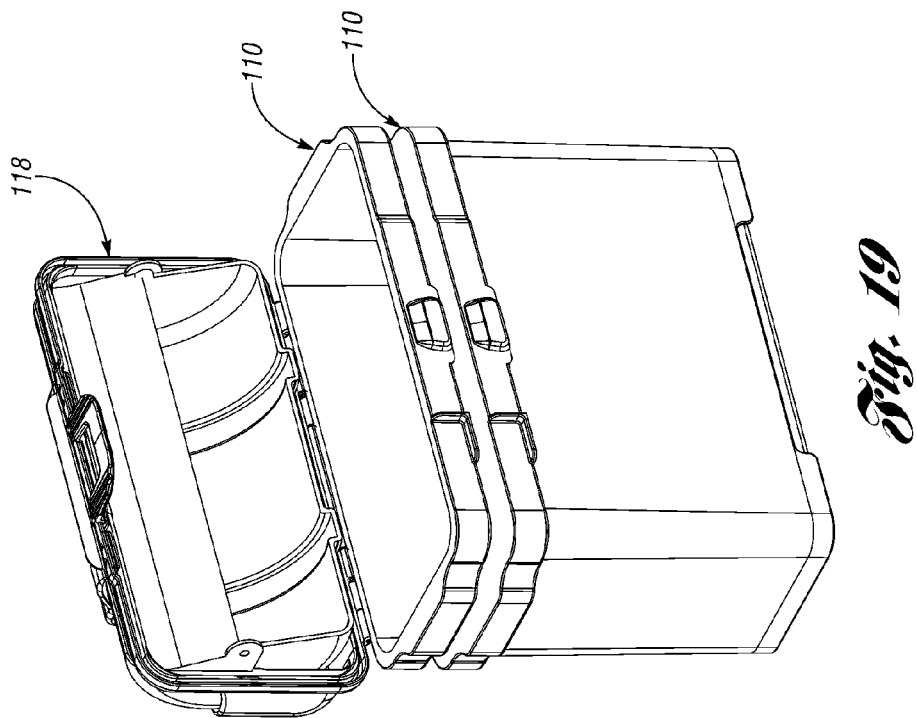
FIG. 19 shows the container of FIG. 12 nested with an identical container.
Figure 18:
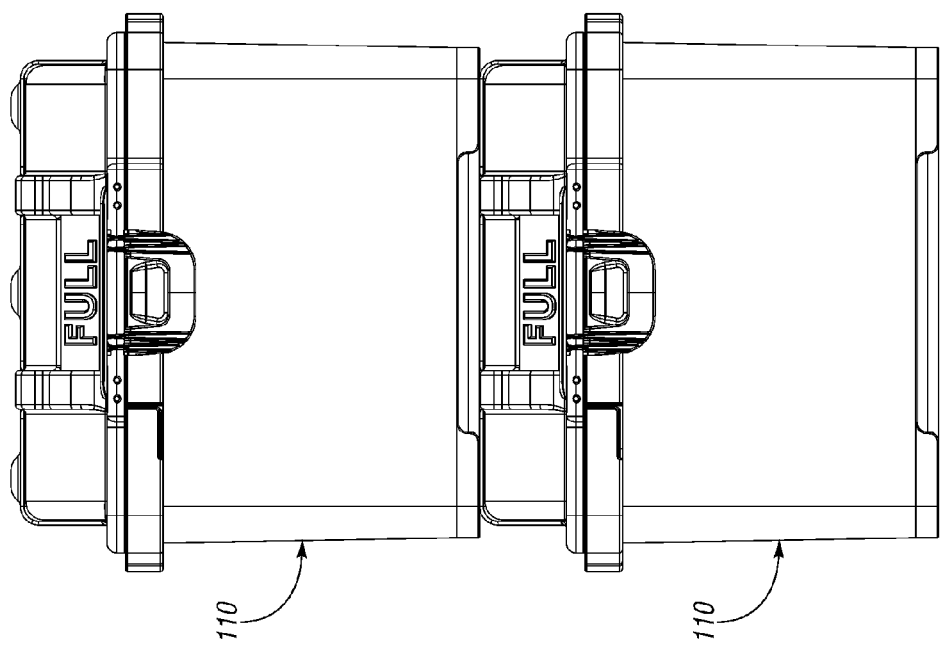
FIG. 18 shows the container of FIG. 12 stacked with an identical container.

As shown in FIG. 18, the containers 110 can be stacked on one another in the closed position. As shown in FIG. 19, the containers 110 can be nested within one another with the lid assemblies 118 in the open position.

Figure 20:
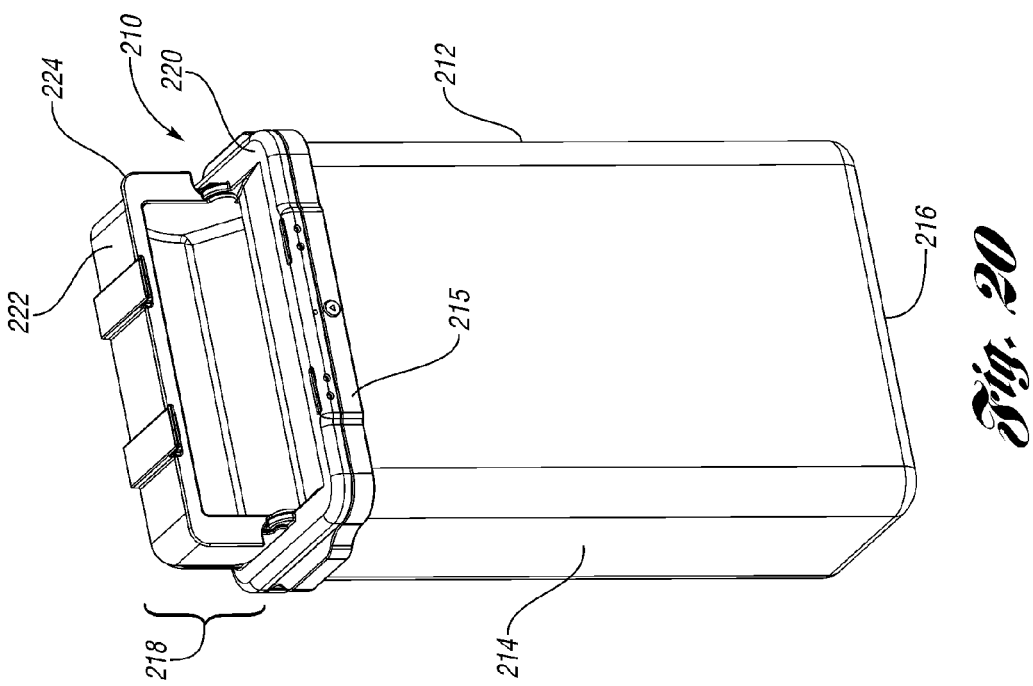
FIG. 20 is a perspective view of a container according to a third embodiment.

A sharps container 210 according to a third embodiment of the present invention is shown in FIGS. 20-24. Referring to FIG. 20, the container 210 includes a body portion 212 having a side wall 214 extending upwardly from the perimeter of a base wall 216. A lip 215 protrudes outwardly and then downwardly from an upper edge of the side wall 214. The container 210 further includes a lid assembly 218 selectively enclosing the opening to the body portion 212. The lid assembly 218 includes a lid portion 220, a lock arm 222 and a sub-lid 224. The lid portion 220 is connected to the lip 215 of the body portion 212. The lock arm 222 and the sub-lid 224 are pivotably connected to the lid 20.

Figure 21:
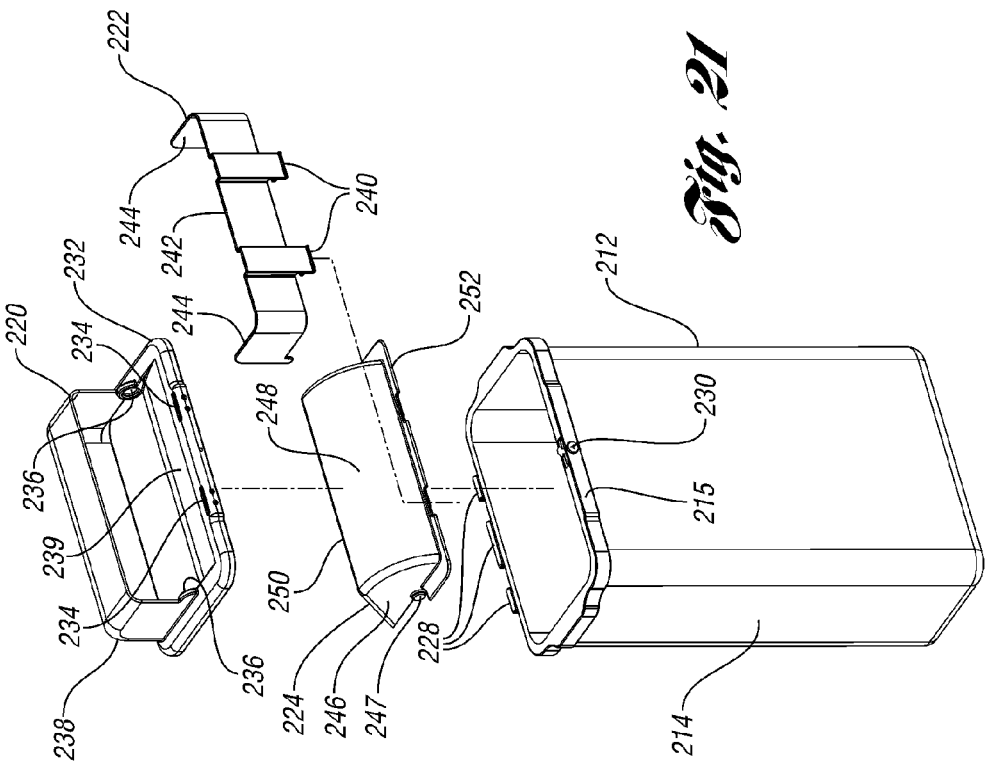
FIG. 21 is an exploded view of the container of FIG. 20.

An exploded view of the container 210 is shown in FIG. 21. The body portion 212 includes hinge members 228 at a rear of the body portion 212 extending from the lip 215. A lock 230 is secured to the lip portion 215 at the front of the body portion 212.

The lid portion 220 includes a perimeter lip portion 232 having a pair of slots 234 formed through a front portion thereof. Pivot recesses 236 are formed in side portions of the lid portion 220. The rear half (approximately) of the lid portion 220 includes a hood 38 extending upwardly from the perimeter lip 232 and forwardly to about a midpoint of the lid portion 220. An upper wall 239 of the lid portion 220 extends from a front portion of the lip 232 and slopes downwardly to an approximate midpoint of the lid portion 220. Thus, an opening is defined between the rearward edge of the upper wall 239 and the back wall of the hood 238.

The lock arm 222 includes a pair of locking tabs 240 extending downwardly from a front wall 242. The front wall 242 is defined between a pair of arms 244, which pivotably connect to the lid portion 220 as shown in FIG. 20.

The sub-lid 224 includes side walls 246 having pivot pins 247 extending therefrom. A concave upper wall 248 joins the two side walls 246 and is connected to a flat lower wall 250. A flange 252 protrudes outwardly from an upper portion of the side walls 246 and the upper edge of the upper wall 248.

Figure 22:
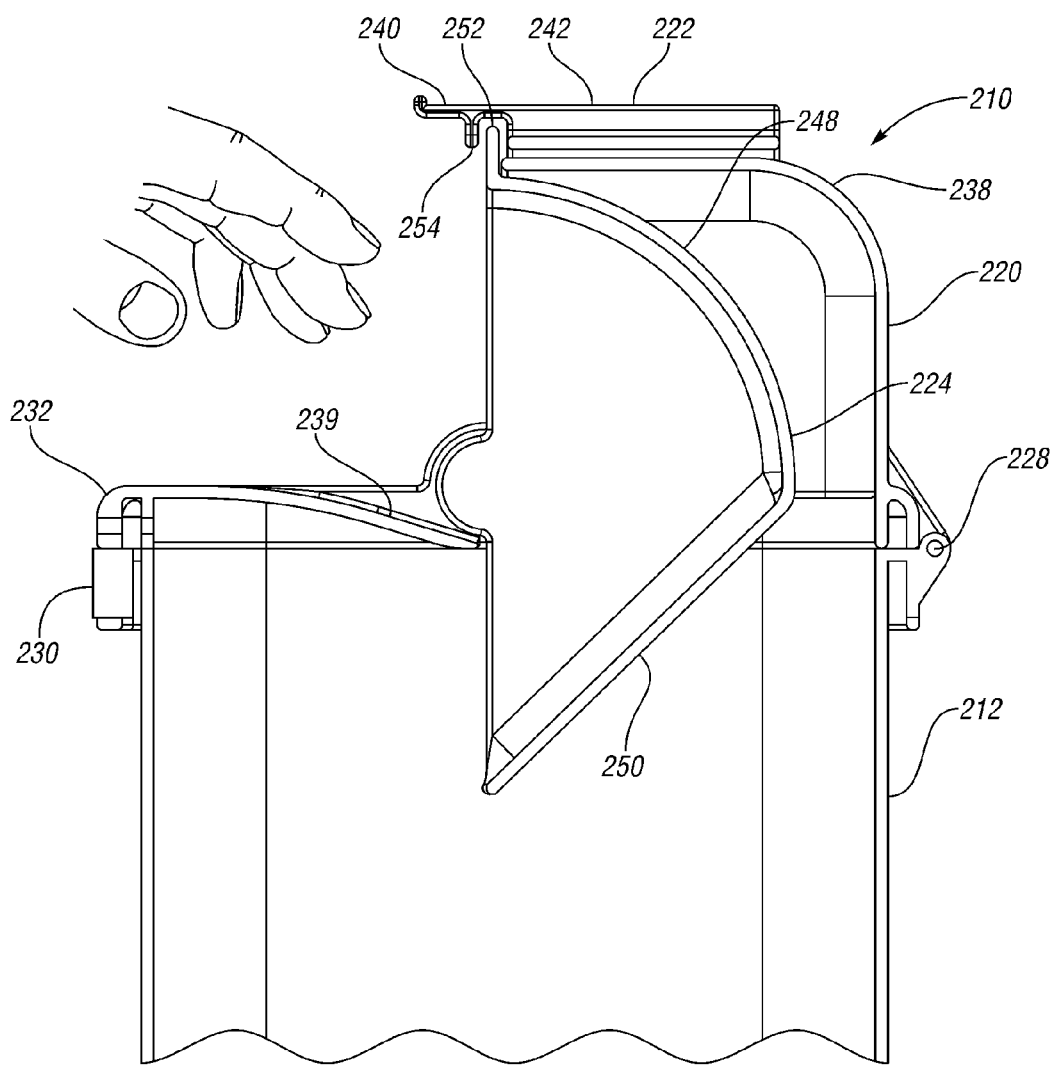
FIG. 22 is a section view through the container of FIG. 20 in the open position.

FIG. 22 is a section view through the container 210 of FIG. 20. In the open position, objects, such as hazardous, sharp medical objects can be deposited through the opening defined between the upper wall 248 of the sub-lid 224 and the upper wall 239 of the lid portion 220. The lower wall 250 of the sub-lid 224 together with the upper wall 239 of the lid portion 220 define a tortuous path that permits small objects to drop into the body portion 212, but prevents a hand from reaching into the body portion 212. The sub-lid 224 remains in the open position due to weight balance and the hinge location. This also causes the sub-lid 224 to automatically rotate down into the closed position if the container 210 falls and rotates upside-down.

Figure 24:
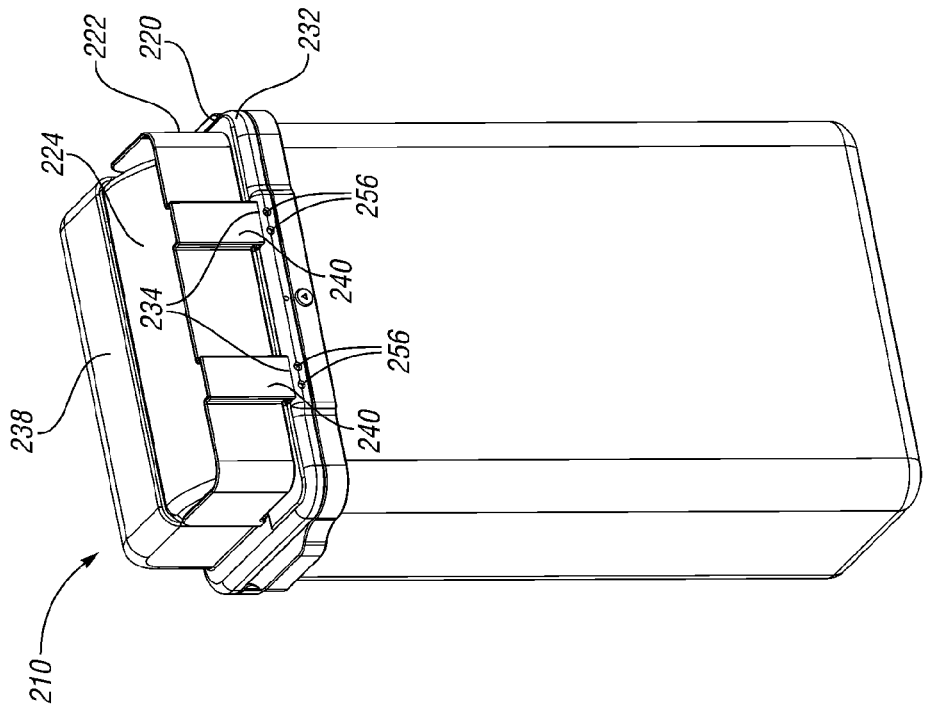
FIG. 24 shows the container of FIG. 23 with the lock arm rotated down to the locked position.
Figure 23:
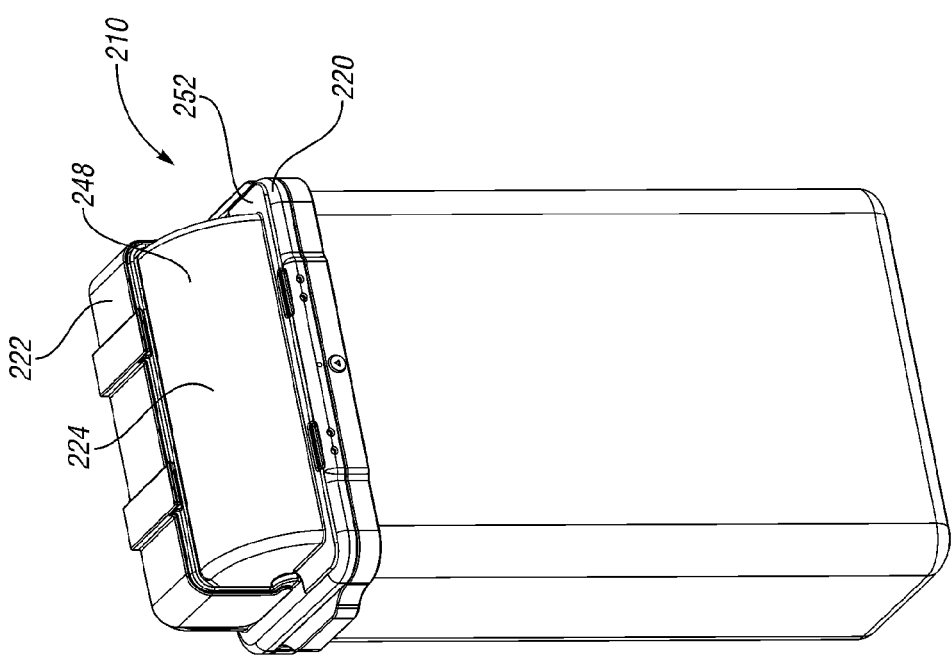
FIG. 23 shows the container of FIG. 20 with the sub-lid rotated to the closed position.

As shown in FIG. 23, the sub-lid 224 can be rotated downward to the closed position. The upper wall 248 of the sub-lid 224 covers the opening between the hood 238 and the upper wall 239 of the lid portion 220 (FIG. 22). The sub-lid 224 can be repeatedly opened and closed in order to place more objects into the body portion 212 of the container 210. When the container 210 is full, the lock arm 222 is rotated downward over the flange 252 of the sub-lid 224, as shown in FIG. 24. The locking tabs 240 snap into the slots 234 in the lip 232 of the lid portion 220, thereby more permanently closing the container 210. The locking arm 222 and sub-lid 224 cannot be opened again without special tools inserted into the small openings 256 formed at the front of the lip 232 of the lid portion 220, in order to release the locking tabs 240. The container 210 loaded with objects would be shipped as shown in FIG. 24 and would be opened at the disposal facility for disposing of the objects therein, possibly washing the container 210 and returning the container 210 for reuse.

FIGS. 25-28 illustrate a container 310 according to a third embodiment of the present invention. The container 310 includes a body portion 312 having a side wall 314 extending upwardly from the periphery of a base wall 316. A lip 315 protrudes outwardly and then downwardly from an upper most edge of the side wall 314. A lid assembly 318 is secured over an opening to the body portion 312. The lid assembly 318 includes a lid portion 320 having a peripheral lip 332, which is selectively latched to the lip 315 of the body portion 312 by a sliding latch member 330, which can be released by sliding the latch member 330 to a release position 333 on the lid portion 320.

Figure 26:
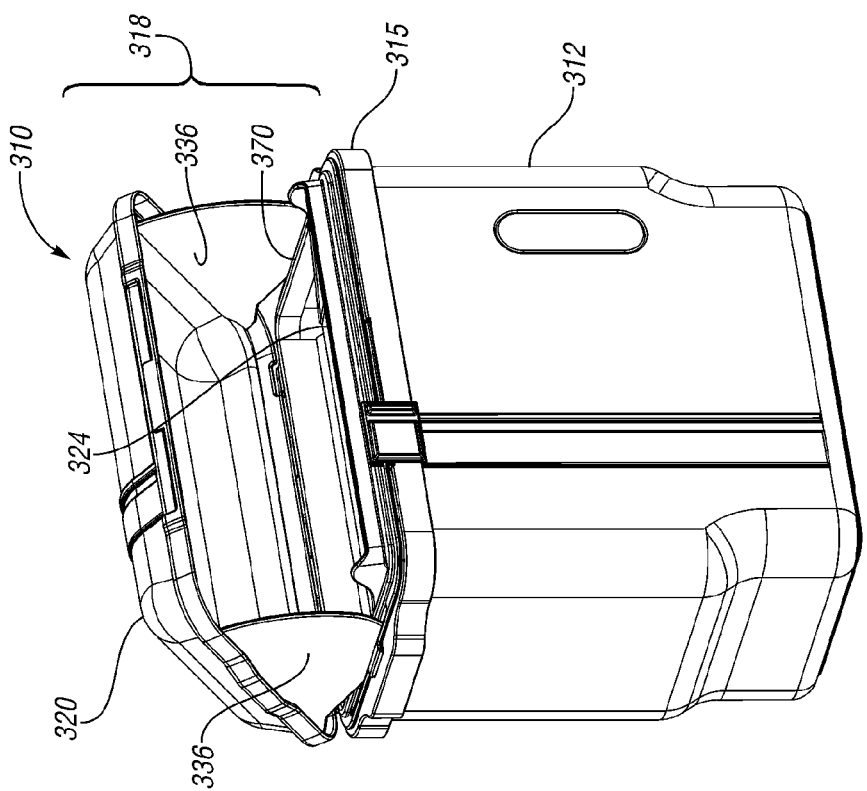
FIG. 26 shows the container of FIG. 25 in the open position.
Figure 25:
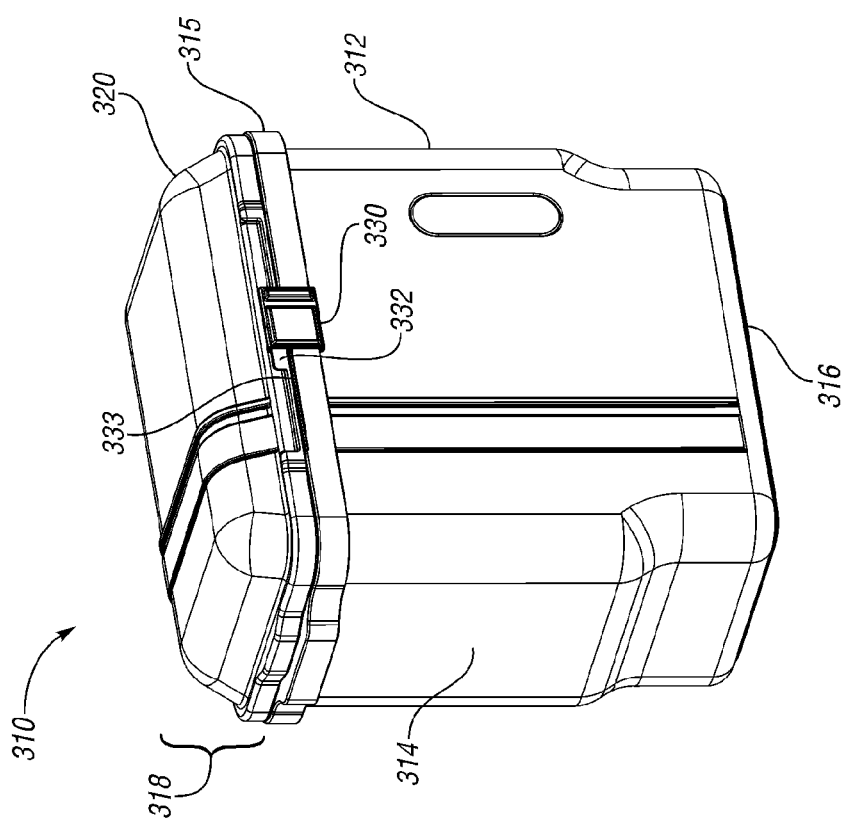
FIG. 25 is a perspective view of a container according to a fourth embodiment in the closed position.

FIG. 26 shows the container 310 in the open position, with the lid portion 320 pivoted upwardly about an axis at its rearward edge. The lid portion 320 includes side walls 336 projecting downwardly into the container 310. A dump tray 324 is pivotably mounted in the mouth of the body portion 312. A guard 370 is also mounted in the mouth of the body portion 312.

FIG. 27 is an exploded view of the container 310. The tray 324 includes a lower wall portion 348 and a pair of opposed pivot pins 347 about which the tray 324 can pivot.

The guard 370 includes a peripheral wall portion 372 having a lip about the periphery thereof. The guard 370 further includes a rear wall 374 extending downwardly and inwardly at an angle. In the embodiment shown, the rear wall 374 is concave.

Figure 28:
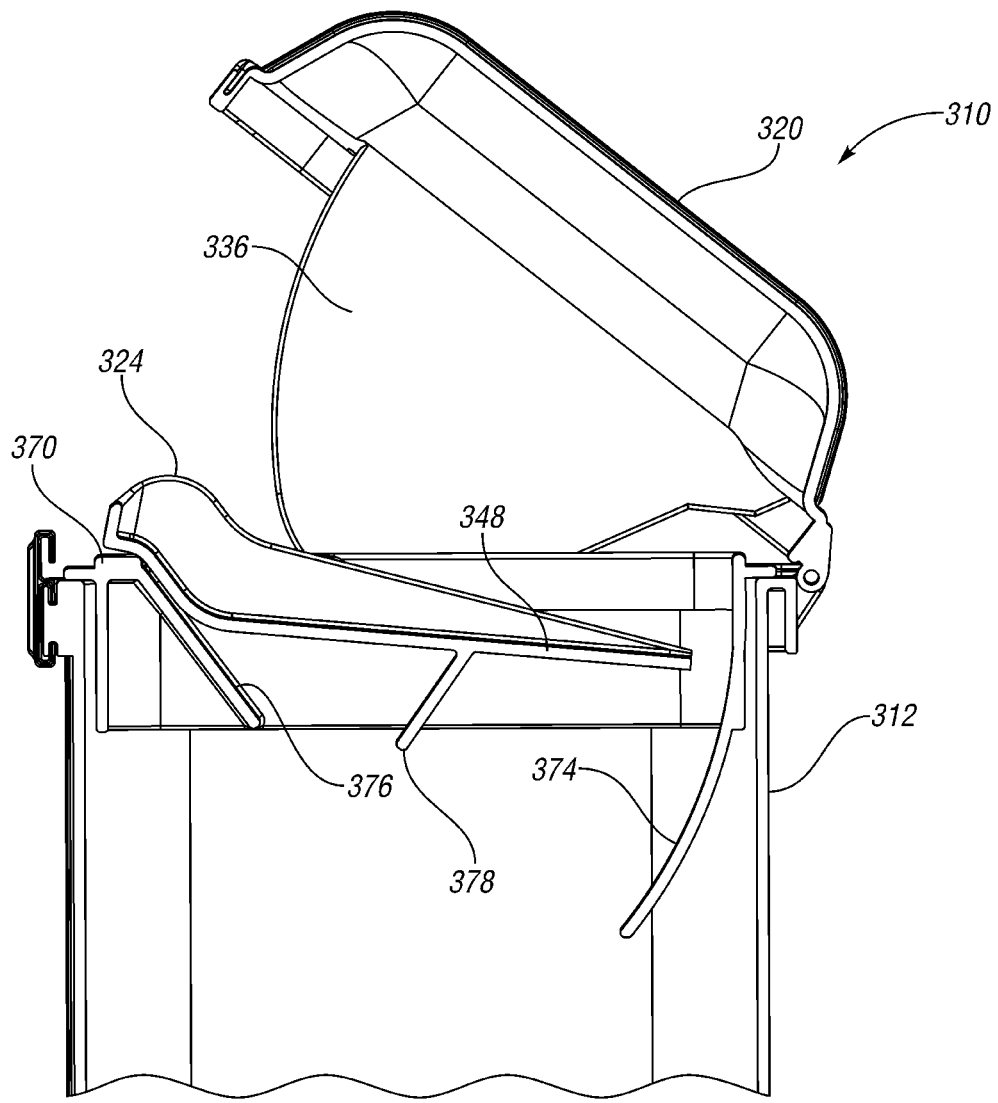
FIG. 28 is a section view through the container of FIG. 26.

Referring to FIG. 28, when the lid portion 320 is opened, an opening is defined between the front edge of the lid portion 320 and the tray 324. An object placed on the lower wall 348 of the tray 324 will cause the tray 324 to tip downwardly, thereby dumping the object into the body portion 312 of the container 310. The wall 348 of the tray 324 together with the rear wall 374 of the guard 370 provide a tortuous path into the body portion 312, thereby preventing a hand from entering the body portion 312. An angled wall 378 extends downwardly from the lower wall 348 of the tray 324 to retain objects in the body portion 312. The guard 370 includes a front wall angled inwardly to provide a stop for the tray 324.

As shown in FIG. 29, the entire lid assembly 318 can be pivoted to the open position as shown, to empty the contents of the container 310 and permit washing.

In accordance with the provisions of the patent statutes and jurisprudence, exemplary configurations described above are considered to represent a preferred embodiment of the invention. However, it should be noted that the invention can be practiced otherwise than as specifically illustrated and described without departing from its spirit or scope.

What is claimed is:
1. A container comprising:
   a body portion including a side wall extending upward from a base wall to define a container interior having an upper opening; and a sub-lid including a wall at least partially covering the upper opening such that an access opening to the container interior is defined by the wall, the wall of the sub-lid including a concave wall portion and a rear wall portion, the sub-lid pivotable relative to the body portion between an open position and a closed position such that the rear wall portion moves rearward when the sub-lid is moved to the closed position, the sub-lid configured to automatically return to the open position from the closed position when released by a user, wherein the access opening is greater when the sub-lid is in the closed position than when the sub-lid is in the open position, and wherein smaller objects can pass through the access opening while the sub-lid is in the open position and larger objects will not fit through the access opening until the sub-lid is moved to the closed position.

2. The container of claim 1 further including an apron extending partially over the upper opening, the access opening defined between the apron and the wall.

3. The container of claim 1 wherein the access opening is less than 1.5" when the sub-lid is in the open position and greater than 1.5" when the sub-lid is in the closed position.

4. The container of claim 1 further including a lid that can be selectively moved to be closed over the sub-lid.

5. The container of claim 1 further including an insert selectively secured to the body proximate the upper opening, the sub-lid pivotably attached to the insert.

6. The container of claim 5 wherein the insert includes an apron extending partially over the upper opening, the access opening defined between the apron and the wall.

7. The container of claim 6 wherein the wall of the sub-lid includes a concave wall portion and a rear wall portion.

8. The container of claim 7 wherein the rear wall portion moves rearward when the sub-lid is moved to the closed position.

9. The container of claim 1 wherein the rear wall portion is angled downwardly in the open position such that smaller objects can slide or roll downward directly on the rear wall portion and then into the body portion when the sub-lid is in the open position, wherein the open position is a fully open position.

10. The container of claim 9 wherein the side wall of the body portion includes a front portion, the container further including an apron extending rearward from the front portion partially over the upper opening, the access opening defined between the apron and the rear wall portion.

11. The container of claim 3 wherein the access opening is about 1.05" when the sub-lid is in the open position.

12. A container comprising:
a body portion including a side wall extending upward from a base wall to define a container interior having an upper opening;
a sub-lid including a wall at least partially covering the upper opening such that an access opening to the container interior is defined by the wall, the sub-lid pivotable relative to the body portion between an open position and a closed position, wherein the access opening is greater when the sub-lid is in the closed position than when the sub-lid is in the open position; and
a lid that can be selectively closed over the sub-lid, wherein the lid includes a pair of pins received in guide tracks projecting upward from the body portion, wherein the pins move within the guide tracks as the lid is moved between an open position and a closed position, the guide tracks including a narrow portion selectively maintaining the lid in an open position.

13. A container comprising:
a body portion including a side wall extending upward from a base wall to define a container interior having an upper opening;
an insert secured to the body portion proximate the upper opening, the insert including an apron extending rearwardly from a front portion of the side wall partially over the upper opening; and
a sub-lid pivotably attached to the insert, the sub-lid including a wall at least partially covering the upper opening such that an access opening to the container interior is defined between the wall and the apron, the sub-lid pivotable relative to the body portion between an open position and a closed position, the sub-lid including a concave wall portion and a rear wall portion, the sub-lid pivotable about an axis offset relative to an center of the concave portion of the sub-lid, such that the rear wall portion moves rearward away from the apron when the sub-lid is pivoted to the closed position.

14. The container of claim 13 further including a lid portion including a hood extending over a portion of the upper opening and over the sub-lid.

15. The container of claim 14 wherein the lid portion is integral with the insert.

16. The container of claim 15 wherein the lid portion and the insert are hingeably connected to the body portion.

17. The container of claim 13 further including a lock arm pivotable between an open position and closed position in which the lock arm locks the sub-lid in the closed position.

18. The container of claim 13 wherein the sub-lid is configured to automatically return from the closed position to the open position when released by a user.

19. The container of claim 18 wherein the rear wall is angled downward below the apron such that smaller objects can slide or roll on the apron and then onto the rear wall and then slide or roll on the rear wall and then into the body portion when the sub-lid is in the open position.

20. The container of claim 19 wherein the open position is a fully open position.

21. A container comprising:
a body portion including a side wall extending upward from a base wall to define a container interior having an upper opening;
an apron extending rearward from a front portion of the side wall partially over the upper opening; and
a sub-lid including a rear wall, the sub-lid at least partially covering the upper opening such that an access opening to the container interior is defined between the rear wall and the apron, wherein the access opening is the narrowest point in a path through the upper opening into the body portion of the container, the sub-lid pivotable relative to the body portion between an open position and a closed position, wherein the rear wall is angled downward below the apron such that smaller objects can slide or roll on the apron and then onto the rear wall and then slide or roll on the rear wall and then into the body portion when the sub-lid is in the open position.

22. The container of claim 21 wherein the sub-lid is configured to automatically return to the open position when released by a user.

23. The container of claim 21 wherein the open position is a fully open position.

* * * * *